United States Patent [19]

Recktenwald et al.

[11] Patent Number: 4,745,285

[45] Date of Patent: May 17, 1988

[54] MULTI-COLOR FLUORESCENCE ANALYSIS WITH SINGLE WAVELENGTH EXCITATION

[75] Inventors: Diether J. Recktenwald, Cupertino; Chia H. Chen, San Jose, both of Calif.

[73] Assignee: Becton Dickinson and Company, Franklin Lakes, N.J.

[21] Appl. No.: 898,685

[22] Filed: Aug. 21, 1986

[51] Int. Cl.$^4$ ............................................. G01N 21/64
[52] U.S. Cl. ........................... 250/458.1; 250/459.1; 250/461.1; 250/461.2; 356/318
[58] Field of Search ............... 250/461.2, 461.1, 459.1, 250/458.1; 356/318

[56] References Cited

U.S. PATENT DOCUMENTS

| | | | |
|---|---|---|---|
| 3,826,364 | 7/1974 | Bonner et al. | 209/3 |
| 4,520,110 | 5/1985 | Stryer et al. | 436/536 |
| 4,542,104 | 9/1985 | Stryer et al. | 436/510 |
| 4,599,307 | 7/1986 | Saunders et al. | 435/34 |

OTHER PUBLICATIONS

M. R. Loken, D. R. Parks, and L. A. Herzenberg, "Two-Color Immunofluorescence Using A Fluorescence-Activated Cell Sorter" *The Journal of Histochemistry and Cytochemistry*, vol. 25, No. 7 (1977), pp. 899-907.

*Primary Examiner*—Janice A. Howell
*Assistant Examiner*—Constantine Hannaher
*Attorney, Agent, or Firm*—Richard J. Rodrick

[57] ABSTRACT

A method for determining one or more characteristics of particles using multiple fluorescence analysis comprises directing an incident light beam at the particles under analysis. The particles include at least three fluorescent markers each having different emission spectra. The incident light beam causes the excitation of the markers by light at a single wavelength whereby different wavelengths of fluorescence are emitted from the particles. Different fluorescence emissions associated with the particles under analysis are simultaneously detected. This method further includes associating the detected fluorescence with one or more characteristics of the particles. An apparatus is also part of the present invention for carrying out the aforementioned method.

19 Claims, 2 Drawing Sheets

MULTI-COLOR FLUORESCENCE ANALYSIS WITH SINGLE WAVELENGTH EXCITATION

BACKGROUND OF THE INVENTION

1. Field of the Invention

The present invention relates to a method and apparatus for determining one or more characteristics of particles using multiple fluorescence analysis, and more particularly, concerns a flow cytometry method and apparatus in which multi-color fluorescence analysis may be performed with single wavelength excitation from a light source.

2. Background Description

There are a number of instruments in which the detection of fluorescent characteristics of particles, cells or the like provides valuable information relating thereto. Fluorescence microscopes, flow cytometers and image microscopes, for example, are some of the instruments wherein the detection of fluorescence provides the investigator or user with data concerning the particles or cells under analysis.

In flow cytometry apparatuses, cells or other particles are caused to flow in a liquid flow stream so as to facilitate the investigation of certain characteristics thereof. In general, a flow cytometry apparatus is useful for identifying the presence of certain cells or particles of interest, enumerating those cells or particles and, in some instances, providing a sorting capability so as to be able to collect those cells or particles of interest. In a typical flow cytometry apparatus, a fluid sample containing cells is directed through the apparatus in a rapidly moving liquid stream so that each cell passes serially, and substantially one at a time, through a sensing region. Cell volume may be determined by changes in electrical impedance as each cell passes through the sensing region. Similarly, if an incident beam of light is directed at the sensing region, the passing cells scatter such light as they pass therethrough. This scattered light has served as a function of cell shape and size, index of refraction, opacity, granularity, roughness and the like. Further, fluorescence emitted by labeled cells, or autofluorescent cells, which have been excited as a result of passing through the excitation energy of the incident light beam is detectable for identification of cells having fluorescent properties. After cell analysis is performed by the flow cytometry apparatus, those cells that have been identified as having the desired properties may be sorted if the apparatus has been designed with such capability.

Instruments such as flow cytometry apparatuses are particularly useful for researchers and investigators studying various responses, reactions and functions of the immune system. Immunofluorescence studies as well as fluorescence immunoassays assist the investigator in identifying and targeting select cells of interest so that disease states, conditions and the like may be properly characterized. In addition to immune system investigations, fluorescence analysis is also quite beneficial in cell biology and morphology investigations, including the study of the substructure of cellular material.

In relying upon fluorescence to provide data and information about cells, the mechanics of performing tests for the fluorescence response is a major consideration in the design of the instrument as well as the results to be obtained. Specifically, the fluorescent markers, whether such markers be fluorescent stains or dyes, are typically excited by light energy. Usually there is an optimal wavelength which provides the greatest level of excitation for the fluorochromatic marker being used. Once excited, fluorescence emission occurs typically at wavelengths different from the wavelength of excitation. Fluorescence analysis instruments, whether fluorescence microscopes, image analyzers or flow cytometers, are generally designed to detect the fluorescence emission at the wavelength of emission maxima where the fluorescence signal is strongest.

Fluorescence analysis of cells or particles in which multiple fluorescence emissions may be simultaneously detected is preferred by many investigators because more information about the cells may be gathered. If an arc lamp is employed as the source of excitation light, the spectrum of light available to excite fluorochromatic markers is rich so that different fluorochromes may be excited by a single light source over a wide range of wavelengths. However, the energy level of light energy available for excitation purposes is generally weak so that the resultant emitted signal from the fluorochromatic markers is difficult to detect and process. Other factors, such as the size of the light emitting elements in the lamps, also affect the resultant signals from the fluorochromatic markers. On the other hand, use of a laser for fluorescence excitation purposes provides a significantly higher intensity of the signal, but the light produced by the laser is monochromatic, i.e., at a single wavelength. This has been a limitation for fluorescence analysis investigations since one laser and associated optical and electrical circuitry have been a practical requirement for each fluorochromatic marker to be detected on the cells or particles. In at least one reported instance, Loken et al., "Two-Color Immunofluorescence Using a Fluorescence-Activated Cell Sorter," the Journal of Histochemistry and Cytochemistry, vol. 25, no. 7, pp 899–907, 1977, a single argon-ion laser provided the excitation energy for the simultaneous excitation of fluorescein and rhodamine. Thus, Loken et al. gained the benefit of using one laser excitation source to obtain information about cells associated with two different fluorochromatic agents.

In order to keep the expense and complexity of fluorescence instruments to a minimum while being able to obtain fluorescence emission data from many different fluorescence markets, it would be desirable to be able to use a light source which provides a single wavelength of excitation (at relatively high intensities) for exciting a plurality of fluorescence markers that emit fluorescence at spectrally separated wavelengths, each of which may be individually detected. Although many fluorescent stains and dyes have been available for DNA studies and cell surface marking, it has been unknown to provide a combination of three or more fluorescent markers which are excitable at a single wavelength and produce fluorescence emissions which are sufficiently spectrally separated so that they may be individually detected. As mentioned above, Loken et al. used an argon-ion laser to provide a single wavelength for the excitation of two dyes. Certain new fluorescent conjugates recently have been described in U.S. Pat. Nos. 4,542,104 and 4,520,110. present invention, therefore, is directed to achieving the desired goals set forth above in which a single wavelength of excitation excites at least three fluorescence markers which may be individually detected.

SUMMARY OF THE INVENTION

A method for determining one or more characteristics of particles using multiple fluorescence analysis comprises directing an incident light beam at particles under analysis. The particles include at least three fluorescent markers each having different emission spectra. The incident light beam causes the excitation of the markers at a single wavelength of light whereby different wavelengths of fluorescence are emitted from the particles. The method includes simultaneously detecting the different fluorescence emissions associated with the particles under analysis, and associating the detected fluorescence with one or more characteristics of the particles.

In a preferred embodiment of the present invention, the method for determining one or more immunofluorescent characteristics of cells or the like using multiple fluorescence analysis, comprises moving cells, substantially one at a time, in a liquid flow stream. The cells include at least three-surface fluorescent markers thereon suitable for immunofluorescence analysis. Each marker has different emission spectra in which the emission maxima are sufficiently spectrally separated so that there is no substantial spectral overlap, or, said another way, so that there is substantial spectral difference between emission maxima. A light beam at a single wavelength is directed from a laser to the cells in the flow stream to excite all of the fluorescent markers whereby different wavelengths of fluorescence are emitted from the cells. Different fluorescence emissions, associated with the cells moving in the flow stream, are simultaneously detected. This detected fluorescence is used to determine one or more characteristics of the cells.

In another aspect of the present invention, an apparatus for determining one or more characteristics of particles using fluorescence analysis comprises means for directing a light beam at particles under analysis in order to excite multiple fluorescence markers on the cells by a single wavelength of light. At least three fluorescence detection means are provided for detecting fluorescence emitted by the particles. The detection means include a select combination of light filter means which permit the simultaneous collection of fluorescence emission of at least three spectrally separated wavelengths. Means are provided for associating the detected fluorescence with one or more characteristics of the particles.

In accordance with the principles of the present invention, multiple fluorescence analysis may be performed by using one light source which provides light energy essentially at a single excitation wavelength, taking into account spectral line width. By using a select combination of fluorescent markers, such as dyes, stains or the like, three or more fluorescence emissions may be stimulated by a single excitation wavelength from the light source, preferably a laser. A select combination of optical filters permits the detection apparatus such as a flow cytometry instrument, to detect the spectrally separated emissions of the different excited fluorescent markers. As long as there is adequate spectral spacing between the emission maxima of the different fluorescent markers, and as long as these same markers may be excited at the selected wavelength, multiple fluorescence detection may be accomplished in accordance with this invention. By using a single wavelength of light for excitation purposes, significant savings are achieved over those instruments which currently rely on two or more sources of light excitation. These savings are not only realized as far as expense, but also in the reduction of complexity of the equipment and operator interface. It is also a benefit of the present invention that the different fluorescence emissions may be detected simultaneously so that the sample under analysis may provide multiple fluorescence information by a single light interrogation mechanism. Other advantages of the present invention will become more apparent from reading the Detailed Description below.

DETAILED DESCRIPTION

Figure 1:
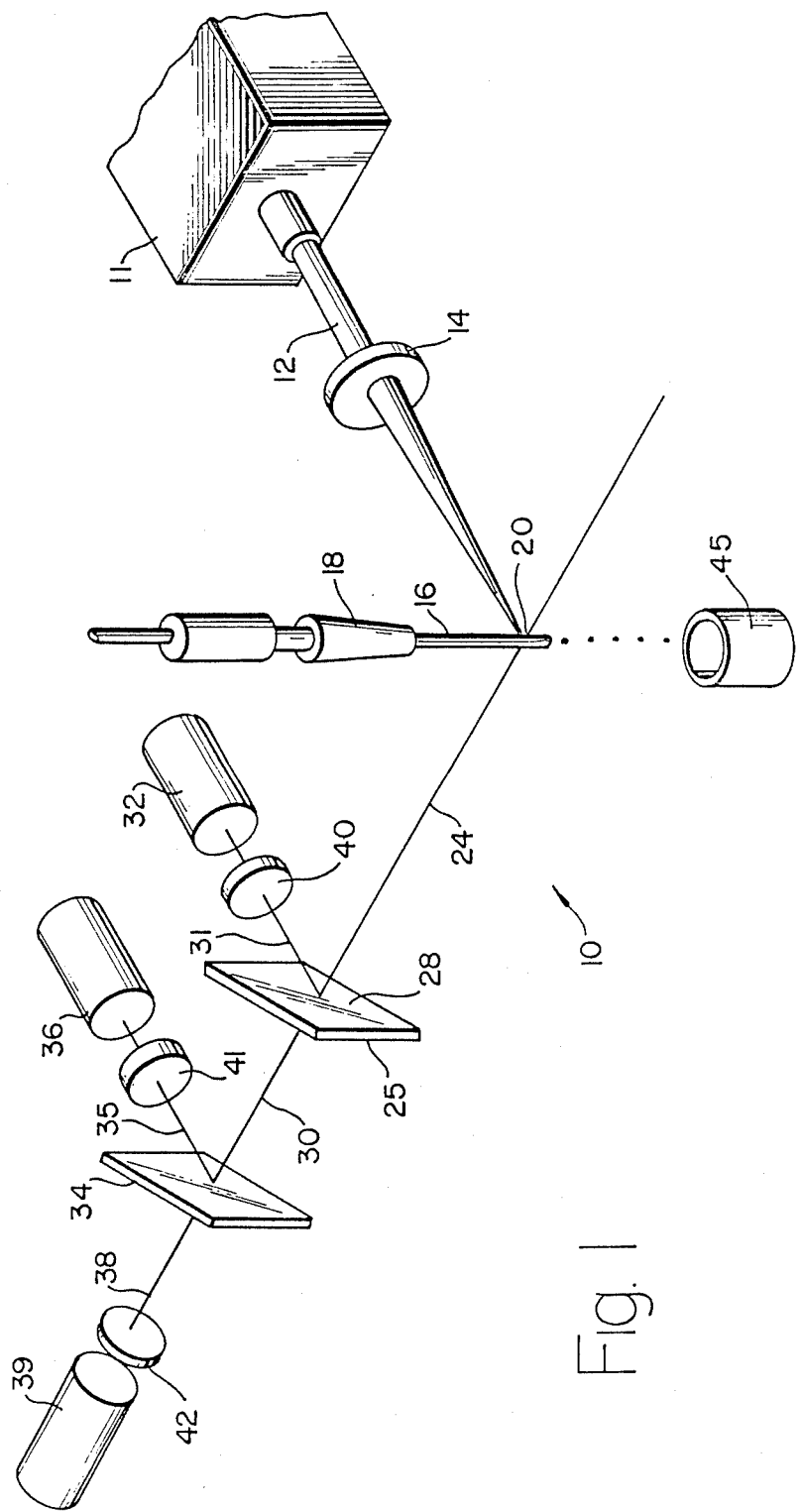
FIG. 1 is a schematic illustration of an embodiment of the optical elements and light paths of a flow cytometry apparatus as one aspect of the present invention for determining one or more characteristics of cells or the like using multiple fluorescence analysis.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

While the present invention will be exemplified by its applicability to a flow cytometry apparatus, as hereinafter described, it is understood that the present invention is useful in a variety of applications including fluorescence immunoassays, fluorescence microscopes, image analyzers and the like. Turning to FIG. 1, the optical and particle flow elements of a flow cytometry apparatus 10 are illustrated. The optical and flow elements of FIG. 1 represent the major components of a flow cytometry apparatus for moving particles, such as cells or the like, in a liquid stream, substantially one at a time, in order assess those particles for specific characteristics thereof. For example, the elements of the apparatus of FIG. 1 may be included in a FACS TM fluorescence-activated cell sorter, marketed by Becton Dickinson Immunocytometry Systems, Mt. View, Calif. The FACS cell sorter analyzes and sorts cell populations on the basis of different light parameters, including fluorescence, in a wide variety of research laboratory applications. In addition to the optical and flow elements to be described in more particular detail herein, and which may be embodied in an instrument such as the FACS cell sorter, other details of a fluorescence detection apparatus useful in conjunction with the present invention are described in U.S. Pat. No. 3,826,364.

As illustrated in FIG. 1, light energy is provided for the present flow cytometry apparatus by a light source 11, which is preferably a laser which generates a collimated beam of light at a singular wavelength. Other light sources may be employed for purposes of the present invention, and filters or the like may be included in order to filter out extraneous wavelengths so that only a single wavelength is directed toward the stream of flowing cells as hereinafter described. Excitation energy is thus provided in the flow cytometry apparatus by a light beam 12 produced by light source 11. Light beam 12 may pass through a focusing lens 14 positioned in the optical path of the light beam. Lens 14 assists in focusing the light beam at a liquid stream 16 containing the particles or cells under investigation.

FIG. 1 also illustrates a nozzle 18 incorporated in the flow cytometry apparatus of the present invention. Cells or particles within liquid stream 16 are caused to flow through nozzle 18. The utilization of a nozzle of this type is well-known and is described, for example, in the aforementioned U.S. Pat. No. 3,826,364. This nozzle provides a hydrodynamically focused flow of cells within a sheath liquid which, along with the stream of cells, comprises liquid flow stream 16. As each cell or particle passes through the adjusted focused light region 20, where light beam 12 intersects liquid stream 16, the light energy of the light beam stimulates the fluorescent markers on those cells which are either autofluorescent or have been stained with a marker, dye or stain receptive to stimulation energy at the wavelength provided by light source 11.

Fluorescence, if emitted by cells energized by the illumination from the light source, may be detected so that information about the cells under investigation may be gathered. In laser-excited flow cytometry, fluorescence is typically collected at an angle whose viewing axis is substantially 90° relative to the excitation axis of the incident light beam from the laser. In FIG. 1, axis 24 represents the 90° viewing axis for the collection of fluorescence.

In order to collect fluorescence at different wavelengths emitted by the cells at the 90° angle from the incident light beam, the fluorescence signals are typically separated or split. This separation may be accomplished by many different techniques such as a dichroic mirror or beam splitter 25. In the embodiment being described, fluorescence travels along axis 24 until it strikes leading face of dichroic mirror 25. Fluorescence in one color region may be reflected by dichroic mirror 25, and the reflected signal then travels along axis 31 so that it may be collected in a photodetector 32. Fluorescence in another color region is transmitted through the dichroic mirror and travels along axis 30. This fluorescence travelling along axis 30 may be further refined or separated by the provision of another dichroic mirror or beam splitter 34. This mirror may be utilized to separate the different color wavelengths of the transmitted fluorescence signal. Thus, and for example, fluorescence in the originally transmitted color region may be reflected by dichroic mirror 34 along axis 35 and collected in an appropriate photodetector 36. Fluorescence in a different color region may be transmitted through dichroic mirror 34 along axis 38 and collected in an appropriate photodetector 39. While not illustrated in FIG. 1, those skilled in the art will appreciate that various lenses, barriers or the like may be employed in conjunction with each of the photodetectors to obtain as pure a signal as possible. In particular, and as seen in FIG. 1, filters 40, 41 and 42 are associated with photodetectors 32, 36 and 39, respectively. These light filters are preferably bandpass filters which filter the fluorescence signals prior to being collected in the respective photodetectors. It is appreciated that, instead of pure bandpass filters, each of these filters may be a combination of short and long pass filters which function in similar fashion to a bandpass filter.

By properly choosing the optical elements for spectrally separating the fluorescent signals, including the choice of dichroic mirrors and filters, many different fluorescent signals may be simultaneously collected at different wavelengths. Thus, although three photodetectors are described in conjunction with FIG. 1, it is within the purview of the present invention to use even more optical filtration elements such as mirrors or filters in order to refine a spectrally rich fluorescence emission signal to spectrally separate the components for individual collection. It is the unique feature of the present invention, however, that while a plurality of fluorescent emissions from the cells or the like may be simultaneously collected, the excitation energy for stimulating fluorescence is provided by a single light source providing a light beam at a single wavelength. To this end, the present invention permits the simultaneous detection of three or more fluorescent emission signals, the fluorescence activity of which is stimulated by a single wavelength of light energy. In order to achieve this desirable result, not only is the selection of the combination of light filter means a factor, but the combination of fluorescent markers on the flowing cells or particles should be chosen to be compatible with the capabilities of the instrument.

Before describing the combination of fluorescent markers and optical filters to achieve the unique results of the present invention, it should be pointed out that particles or cells in liquid stream 16 may be collected in an appropriate container 45, or, perhaps, may be sorted and collected in different containers if the flow cytometry apparatus employs a sorting capability. Once the above-described photodetectors receive the fluorescent light signals, the information gained thereby may be further utilized. The various photodetectors may be well-known photomultiplier tubes or similar devices which convert light signals into electrical impulses so that the light thereby detected may be associated with the cells flowing through the apparatus. The electrical signals from the photodetectors are typically fed to the electronics (not shown) of the apparatus for purposes of display, storage or further processing so that one or more characteristics of the cells under analysis may be determined.

In choosing the combination of fluorescent markers for the cells to be analyzed, as well as the optical filters and related elements for spectrally separating and collecting different fluorescent signals, there are a number of factors which should be taken into account. For example, the fluorescent markers should be selected so that they may all be excited by the light energy at a single wavelength, but the fluorescent emissions should be sufficiently spectrally separated to permit individual detection without substantial spectral overlap. Along these lines, it is preferred that the spectral spacing between the emission maxima of adjacent fluorescent markers along the fluorescent spectrum should be at least 15 nm. Then, of course, the dyes or fluorescent markers should be selected so as to be compatible with the excitation line of energy from the light source which is part of analysis instrument. For example, an argon-ion laser includes a typical line of energy output for fluorescence excitation purposes at 488 nm. At this single wavelength, there are many available dyes, cell surface stains or combinations of stains which are excitable and which produce emissions at different wavelengths of light so that they may be individually detected.

The following examples are illustrative but not limitative of the principles and features of the present invention.

EXAMPLE I

Figure 2:
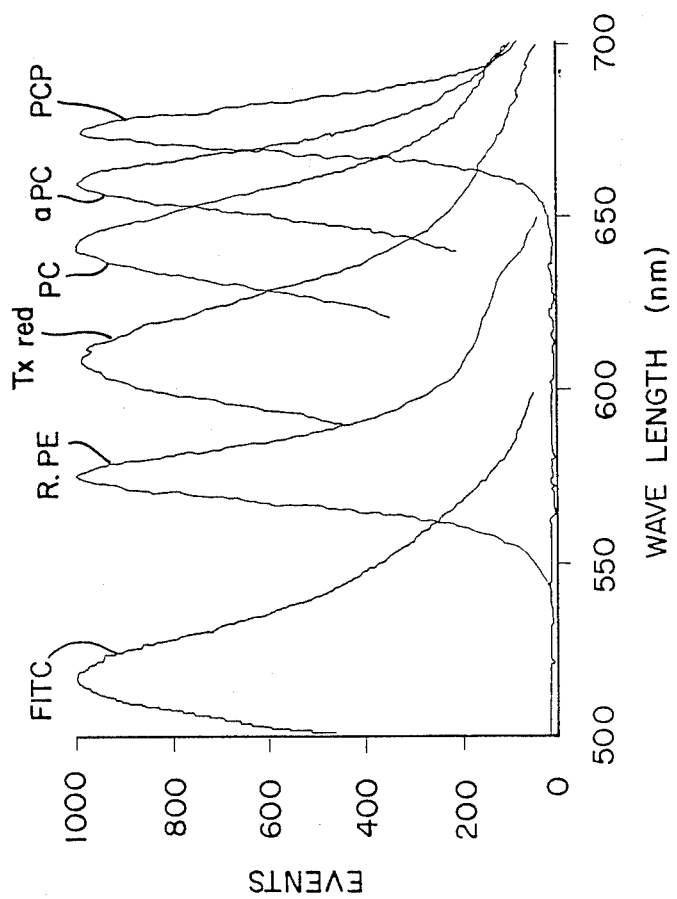
FIG. 2 is a graphical display of spectra illustrating fluorescence emission intensities versus wavelength (nanometers) for six different fluorescence markers excited by light at a single wavelength in accordance with the principles of the present invention.

A cell sample was prepared with six different immunofluorescent stains. Since different types of cells, subsets of those cells and substructures of those subsets have different stains associated therewith, the detection of these multiple fluorescence signals provides significant information about the nature of the cells being investigated. In this test, the immunofluorescent stains were the following: fluorescein isothiocyanate (FITC), phycoerythrin (PE), Texas red tandem, phycocyanin tandem (PC), allo-phycocyanin tandem (aPC), and peridinin-chlorophyll protein (PCP). The cell sample which includes cells stained with these fluorescent markers was passed through a flow cytometry apparatus similar to the apparatus described above. The light source was an argon-ion laser with a line of energy output for excitation purposes at 488 nm. In order to detect the six different fluorescence emissions stimulated by the excitation energy from the laser, six different photodetectors were used in the instrument. A select combination of optical elements and filters was chosen for spectrally separating the fluorescence emissions for individual collection. Bandpass filters were used at each photodetector with the following characteristics: 525 nm for collection of FITC; 575 nm for collection of PE; 610 nm for collection of Texas red; 640 nm for collection of PC; 660 nm for collection of aPC; and 680 nm for collection of PCP. The flow cytometry instrument was programmed to display a histogram in which the number of events for each fluorescent stain is represented as a function of wavelength. FIG. 2 illustrates the emission characteristics of the six fluorescent markers, all of which were excited at 488 nm, and all of which may be detected simultaneously with an instrument capable of handling this many parameters. It can be seen in FIG. 2 that there is sufficient spectral spacing between the emission maxima so that there is no substantial spectral overlap and so that ready identification of the different fluorescent markers may be made.

EXAMPLE II

A cell sample was prepared in similar fashion to the preparation of Example I using the following stains: PE, Texas red, PC, aPC, and PCP. When exposed to excitation energy at 543 nm using a helium neon laser, at 530 nm using a YAG laser or at 546 nm using a mercury arc lamp, all of these stains were excited and the resultant fluorescent emissions detected without substantial spectral overlap. Similar results were obtained using the same light sources and the same dyes, in which the energy lines of excitation from the light sources were between 529 and 550 nm.

EXAMPLE III

A cell sample was prepared similar to the sample of Example I, using the following five stains: PE, PE-Texas red tandem, PE-PC tandem, PE-aPC tandem, and PCP. When exposed to excitation energy at 543 nm provided by a helium neon laser, at 530 nm using a YAG laser or at 546 nm using a mercury arc lamp, all dyes were excited and their fluorescence emissions separately detected without substantial spectral overlap.

EXAMPLE IV

A cell sample was prepared similar to Example I, in which the following combination of stains was employed: Coumarin (COU), COU-PE, COU-PE-Texas red, COU-PE-CPC, COU-PE-aPC, and PCP. When exposed to a line of light excitation at 442 nm provided by a helium cadmium laser, all of these stains become excited and their fluorescence emissions may be detected simultaneously without substantial spectral overlap.

EXAMPLE V

The cell sample of Example IV was repeated in which the following DNA dyes were substituted for two of the original stains: Amino-actinomycin-D and LDS dye. The results of this test were similar to those obtained in Example IV.

Thus, the present invention provides a method and apparatus for multi-color fluorescence analysis using single wavelength excitation as the source of energy for stimulating a fluorescence response. The simultaneous collection of a large number of fluorescence signals, stimulated by a single high intensity light source such as a laser, significantly enhances the gathering of information about cells or particles under investigation, particularly for immunoassays, immunofluorescence analysis and image microscopy.

What is claimed is:

1. A method for determining one or more characteristics of cells or the like using multiple fluorescence analysis comprising:
    moving cells, substantially one at a time, in a liquid flow stream, said cells including at least three fluorescent markers each having different emission spectra wherein the markers, when excited, produce emission maxima sufficiently spectrally separated to permit detection thereof without substantial spectral overlap;
    directing an incident light beam of a single wavelength at the cells in said flow stream to excite all of the fluorescent markers with the single wavelength of light such that different wavelengths of fluorescence are emitted from said cells;
    spectrally separating with optical elements the different wavelengths of emitted fluorescence to simultaneously refine the emitted fluorescence to enable the separate detection of the different wavelengths;
    simultaneously detecting the three or more different fluorescence emissions associated with the cells moving in the flow stream; and
    using said detected fluorescence to determine one or more characteristics of said cells.

2. The method of claim 1 wherein the fluorescent markers on said cells are cell surface markers suitable for immunofluorescence analysis.

3. The method of claim 2 wherein there are at least four fluorescent markers associated with the cells, at least one of said markers being a dye for providing fluorescence analysis of the interior structure of the cells.

4. The method of claim 3 wherein said dye is a DNA dye.

5. The method of claim 4 wherein the spectral spacing between the emission maxima of adjacent fluorescent markers along the fluorescence spectrum is at least 15 nm.

6. The method of claim 1 wherein the light beam is provided by a laser which generates a wavelength of excitation light at 488 nm.

7. The method of claim 6 wherein the fluorescent markers are selected from the group of dyes consisting of fluorescein, phycoerythrin, Texas red, phycocyanin, allo-phycocyanin, peridinin-chlorophyll protein and dyes in tandem with any of the foregoing.

8. The method of claim 7 wherein there are four fluorescent markers selected from said group.

9. The method of claim 7 wherein there are five fluorescent markers selected from said group.

10. The method of claim 7 wherein there are six fluorescent markers selected from said group.

11. A method for determining one or more characteristics of particles using multiple fluorescence analysis comprising:
directing an incident light beam at particles under analysis, the particles including at least three fluorescent markers each having different emission spectra, but each marker being excitable by light at the same wavelength, said incident light beam causing the excitation of said markers such that spectrally different wavelengths of fluorescence are emitted from said particles without substantial spectral overlap;
spectrally separating with optical elements the different wavelengths of emitted fluorescence to simultaneously refine the emitted fluorescence to enable the separate detection of the different wavelengths;
simultaneously detecting the three or more different fluorescence emissions associated with the particles under analysis; and
associating said detected fluorescence with one or more characteristics of said particles.

12. A method for determining one or more immunofluorescent characteristics of cells or the like flowing in a liquid stream using multiple fluorescence analysis comprising:
moving cells, substantially one at time, in a liquid flow stream, said cells including at least three cell-surface fluorescent markers thereon suitable for immunofluorescence analysis, each marker having different emission spectra in which the emission maxima are sufficiently spectrally separated so that there is no substantial spectral overlap;
directing a light beam of a single wavelength at the cells in said flow stream to excite all of the fluorescent markers such that different wavelengths of fluorescence are emitted from said cells;
spectrally separating with optical elements the different wavelengths of emitted fluorescence to enable the separate detection of the different wavelengths;
simultaneously detecting the three or more different fluorescence emissions associated with the cells moving in the flow streams; and
using said detected fluorescence to determine one or more characteristics of said cells.

13. The method of claim 12 wherein the flourescent markers are chosen from a select combination of cell-surface fluorescent markers excitable by a single wavelength of light.

14. An apparatus for determining one or more characteristics of cells or the like flowing in a liquid stream using multiple fluorescence analysis comprising:
means for moving cells, substantially one at a time, in a liquid flow stream;
means for directing a light beam at the cells in said flow stream in order to excite multiple fluorescence markers on said cells by a single wavelength of light;
at least three fluorescence detection means for detecting spectrally separated fluorescence without substantial spectral overlap emitted by the cells moving the flow stream, each detection means including a select combination of optical light filter means which permit the simultaneous collection of spectrally separate fluorescence emission of at least three spectrally wavelengths; and
means for using said detected fluorescence to determine one or more characteristics of said cells.

15. The apparatus of claim 14 wherein said means for directing light includes a laser.

16. The apparatus of claim 15 wherein the select combination of filter means includes filters selected from the group of filters which permit light to pass therethrough at wavelengths at least 15 nm spectrally spaced from each other.

17. The apparatus of claim 15 wherein the laser provides a wavelength of excitation light at 480 nm.

18. The apparatus of claim 17 wherein the select combination of light filter means includes filters selected from the group of filters which permit light at wavelengths of essentially 525 nm, 575 nm, 610 nm, 630 nm, 660 nm and 680 nm to pass therethrough for collection in the respective detection means.

19. An apparatus for determining one or more characteristics of particles using multiple flourescence analysis comprising:
means for directing a light beam at particles under analysis in order to excite multiple flourescence markers on said cells by a single wavelength of light;
at least three fluorescence detection means for detecting spectrally separated fluorescence without substantial spectral overlap emitted by the particles, each detection means including a select combination of optical light filter means which permit the simultaneous collection of spectrally separate fluorescence emission of at least three spectrally separated wavelengths; and
means for associating said detected fluorescence with one or more characteristics of said particles.

* * * * *

REEXAMINATION CERTIFICATE (1768th)
United States Patent [19]
Recktenwald et al.

[11] B1 4,745,285

[45] Certificate Issued Aug. 11, 1992

[54] MULTI-COLOR FLUORESCENCE ANALYSIS WITH SINGLE WAVELENGTH EXCITATION

[75] Inventors: Diether J. Recktenwald, Cupertino; Chia H. Chen, San Jose, both of Calif.

[73] Assignee: Becton, Dickinson and Company

Reexamination Request:
No. 90/002,459, Oct. 2, 1991

Reexamination Certificate for:
Patent No.: 4,745,285
Issued: May 17, 1988
Appl. No.: 898,685
Filed: Aug. 21, 1986

[51] Int. Cl.⁵ .................................... G01N 21/64
[52] U.S. Cl. ........................ 250/458.1; 250/459.1; 250/461.1; 250/461.2; 356/318

[56] References Cited

U.S. PATENT DOCUMENTS

4,599,307  7/1986  Saunders et al. ............... 435/34

OTHER PUBLICATIONS

Lewis L. Lanier and Michael R. Loken, "Human lymphocyte subpopulations identified by using three-color immunofluorescence and flow cytometry analysis: Correlation of Leu-2, Leu-3, Leu-7, Leu-8, and Leu-11 cell surface antigen expression," *Journal of Immunology*, vol. 132, No. 1 (1984) pp. 151-156.

Stephen Haskill, Susanne Becker, Tim Johnson, Dominic Marro, Kay Nelson and Roy H. Propst, "Simultaneous Three Color and Electronic Cell Volume Analysis with a Single UV Excitation Source," *Cytometry*, [Volume, number and date illegible, probably published in 1983], pp. 359-366 [©Society for Analytical Cytology].

Table of References to Practical Flow Cytometry (2d edit 1988) H. Shapiro.

*Primary Examiner*—Constantine Hannaher

[57] ABSTRACT

A method for determining one or more characteristics of particles using multiple fluorescence analysis comprises directing an incident light beam at the particles under analysis. The particles include at least three fluorescent markers each having different emission spectra. The incident light beam causes the excitation of the markers by light at a single wavelength whereby different wavelengths of fluorescence are emitted from the particles. Different fluorescence emissions associated with the particles under analysis are simultaneously detected. This method further includes associating the detected fluorescence with one or more characteristics of the particles. An apparatus is also part of the present invention for carrying out the aforementioned method.

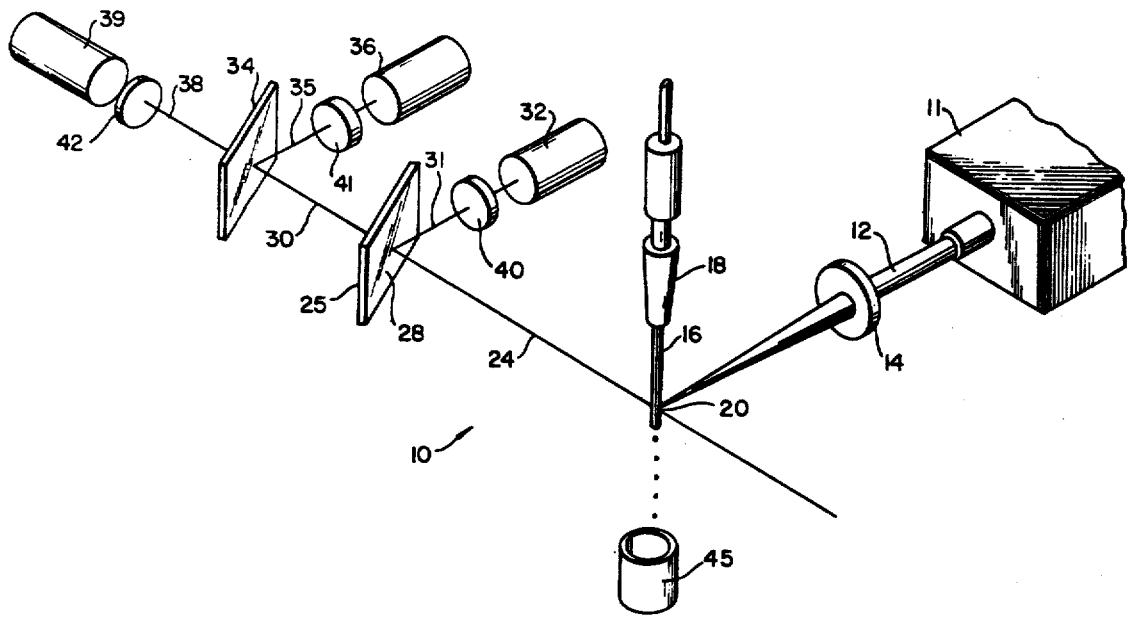

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 44–68:

In order to keep the expense and complexity of fluorescence instruments to a minimum while being able to obtain fluorescence emission data from many different fluorescence [markets] *markers*, it would be desirable to be able to use a light source which provides a single wavelength of excitation (at relatively high intensities) for exciting a plurality of fluorescence markers that emit fluorescence at spectrally separated wavelengths, each of which may be individually detected. Although many fluorescent stains and dyes have been available for DNA studies and cell surface marking, it has been unknown to provide a combination of three or more fluorescent markers which are excitable at a single wavelength and produce fluorescence emissions which are sufficiently spectrally separated so that they may be individually detected. As mentioned above, Loken et al. used an argon-ion laser to provide a single wavelength for the excitation of two dyes. Certain new fluorescent conjugates recently have been described in U.S. Pat. Nos. 4,542,104 and 4,520,110. *The* present invention, therefore, is directed to achieving the desired goals set forth above in which a single wavelength of excitation excites at least three fluorescence markers which may be individually detected.

AS A RESULT OF REEXAMINATION, IT HAS BEEN DETERMINED THAT:

Claims 1, 2, 6, 7, 11, 15 and 19 having been finally determined to be unpatentable, are cancelled.

Claims 3, 8–10, 12 13 and 14 are determined to be patentable as amended.

Claims 4, 5, 16, 17 and 18, dependent on an amended claim, are determined to be patentable.

3. The method of claim [2] *12* wherein there are at least four fluorescent markers associated with the cells, [at least] one of said markers being a dye for providing fluorescence analysis of the interior structure of the cells.

8. The method of claim [7] *13* wherein there are four fluorescent markers selected from said group.

9. The method of claim [7] *13* wherein there are five fluorescent markers selected from said group.

10. The method of claim [7] *13* wherein there are six fluorescent markers selected from said group.

12. A method for determining one or more immunofluorescent characteristics of cells or the like flowing in a liquid stream using multiple fluorescence analysis comprising:

combining the cells with a mixture comprising at least three immunofluorescent markers wherein each marker has a different emission spectra which, when excited, produces emission maxima sufficiently spectrally separated to permit detection thereof without substantial overlap;

moving cells, substantially one at *a* time, in a liquid flow stream[, said cells including at least three cell-surface fluorescent markers thereon suitable for immunofluorescence analysis, each marker having different emission spectra in which the emission maxima are sufficiently spectrally separated so that there is no substantial spectral overlap];

directing [a] *laser* light [beam] of a single wavelength *of approximately 488 nm* at the cells in said flow stream to excite all the fluorescent markers such that different wavelengths of fluorescence are emitted from said cells;

spectrally separating with optical elements the different wavelengths of emitted fluorescence *to simultaneously refine the emitted fluorescence to* enable the separate detection of the different wavelengths;

simultaneously detecting the three or more different fluorescence emissions associated with the cells moving in the flow [streams] *stream*; and using said detected fluorescence to determine one or more characteristics of said cells.

13. The method of claim 12 wherein the [flourscent] *fluorescent* markers are [chosen from a select combination of cell-surface fluorescent markers excitable by a single wavelength of light] *selected from the group of dyes consisting of fluorescein, phycoerythrin, Texas red, phycocyanin, allo-phycocyanin, perdininchlorophyll protein and dyes in tandem with any of the foregoing.*

14. An apparatus for determining one or more characteristics of cells or the like flowing in a liquid stream using multiple fluorescence analysis, *wherein the cells have been combined with a mixture comprising at least three immunofluorescent markers wherein each marker has a different emission spectra which, when excited, produces emission maxima sufficiently spectrally separated to permit detection thereof without substantial overlap,* comprising:

means for moving cells, substantially one at a time, in a liquid flow stream;

means for directing a *laser* light beam at the cells in said flow stream in order to excite multiple fluorescent markers on said cells by a single wavelength of light *of approximately 488 nm;* at least three fluorescence detection means for detecting spectrally separated fluorescence without substantial overlap emitted by the cells moving *in* the flow stream, each detection means including a select combination of optical light [filter] *filters* means which permit the simultaneous collection of spectrally separate fluorescence emission of at least three [spectrally] *spectral* wavelengths; and means for using said detected fluorescence to determine one or more characteristics of said cells.

* * * * *